(12) United States Patent
Owen et al.

(10) Patent No.: US 6,697,154 B2
(45) Date of Patent: Feb. 24, 2004

(54) MICROVIA INSPECTION SYSTEM (75) Inventors: Mark Douglas Owen, Beaverton, OR (US); Adrian Boyle, Monasterevin (IE); Niall Dorr, Dublin (IE); James Mahon, Dublin (IE); Peter Conlon, Dublin (IE)

(73) Assignee: MV Research Limited, Dublin (IE)

( * ) Notice: Subject to any disclaimer, the term of this patent is extended or adjusted under 35 U.S.C. 154(b) by 59 days.

(21) Appl. No.: 09/986,961

(22) Filed: Nov. 13, 2001

(65) Prior Publication Data

US 2002/0027654 A1 Mar. 7, 2002

Related U.S. Application Data (63) Continuation of application No. PCT/IE00/00061, filed on May 11, 2000.

(30) Foreign Application Priority Data

May 14, 1999  (IE) ................................................ 990391

(51) Int. Cl.[7] .......................... G01N 21/88; H04Q 9/47; G06K 9/00
(52) U.S. Cl. ................ 356/237.5; 356/237.6; 348/126; 382/149
(58) Field of Search .......................... 356/237.5, 237.6, 356/626; 382/148, 147, 149; 348/126; 250/559.45

(56) References Cited

U.S. PATENT DOCUMENTS

| | | | | |
|---|---|---|---|---|
| 4,560,273 A | * | 12/1985 | Ando et al. | 356/237.6 |
| 4,647,208 A | * | 3/1987 | Bieman | 356/615 |
| 5,214,712 A | * | 5/1993 | Yamamoto et al. | 382/149 |
| 5,301,012 A | | 4/1994 | King et al. | 356/398 |
| 5,347,591 A | | 9/1994 | Onishi et al. | 382/8 |
| 5,365,341 A | | 11/1994 | Sugawara | 356/394 |
| 5,610,710 A | * | 3/1997 | Canfield et al. | 356/237.6 |

FOREIGN PATENT DOCUMENTS

| | | |
|---|---|---|
| EP | 0459489 A2 | 12/1991 |
| EP | 0467149 A2 | 1/1992 |

* cited by examiner

*Primary Examiner*—Zandra V. Smith
(74) *Attorney, Agent, or Firm*—Jacobson Holman PLLC (57) ABSTRACT

A system has a projection lens directing on-axis light and low level LEDs directing light to blind microvias. A high resolution camera captures blind microvia images and an image processor recognizes defects according to classifications according to reflected light area and centroid position. The lens is telecentric for particularly effective image capture in blind microvias. The system also has an array of 6000 back lighting LEDs providing illumination for capture of images by a camera. These images are analyzed by the image processor to detect defects such as blocked through microvias.

21 Claims, 7 Drawing Sheets

| Classification | After Lazer | Image |
|---|---|---|
| 54 Good Via |  |  |
| 55 Overdrilled or Blocked Via |  |  |
| 56 Underdrilled Via |  |  |
| 57 Bad Via |  |  |

Fig. 10

MICROVIA INSPECTION SYSTEM

This is a continuation of PCT/IE00/00061 filed May 11, 2000 and published in English.

FIELD OF THE INVENTION

The invention relates to inspection of microvias in circuit boards.

PRIOR ART DISCUSSION

In recent years there has been a very rapid move towards increased miniaturisation of circuits because of demands of industries such as the mobile telecommunications industry. Where multi-layer circuit boards are used there id frequent use of "blind" vias which do not extend fully through the board but instead penetrate part of the depth of the board to reach an internal layer to make an electrical connection. Whether the board is multi-layered or not, there is also frequent use of through vias to make connections from the front surface to the back surface.

With increased miniaturisation and higher circuit densities, the sizes of the vias has been decreasing and they are now generally referred to as "microvias". Typically, the sizes range between 20 $\mu$m and 75 $\mu$m. The technologies to drill microvias involve use of high-precision laser beams. The laser may be of the CO2 or UVYAG types.

While these technologies are quite effective, in full-scale production various defects may arise due to problems such incorrect setting of drilling equipment, loading of incorrect files, incorrect handling of the circuit board, of residual debris in or near the microvia. When defects arise the board panels are often too expensive to scrap and expensive re-work is required.

Existing inspection systems have been developed for inspection of components and solder paste and are not sufficiently effective for detection of defective microvias. As a result, defective microvias are often not detected until full functional tests are carried out downstream. This is a very expensive way to detect such defects. Also, in some cases the defects go un-noticed until a fault arises in the field.

OBJECTS OF THE INVENTION

It is an object of the invention to provide an inspection system for detection of defective microvias in an effective manner in a full-scale production environment.

SUMMARY OF THE INVENTION

According to the invention, there is provided a microvia inspection system comprising:
means for supporting a circuit board in a circuit board plane;
a top lighting means comprising means for illuminating the top of a circuit board at an angle of greater than 50° to the circuit board plane;
a camera;
a controller comprising:
 means for reading circuit board target data to determine target locations and sizes of microvias, and for controlling the top lighting means and the camera to capture images of said microvias, and
 image processing means for determining quality of the microvias according to intensity and distribution of reflected light in the images.

In one embodiment, the image processing means comprises means for recognising a blind microvia as defective if a measured area of reflected light is below a threshold area.

In one embodiment, the image processing means comprises means for recognising a blind microvia as defective if a measured centroid of the reflected light is offset from a target location to an extent greater than a threshold distance.

In another embodiment, the image processing means comprises means for recognising a microvia as defective because of under-drilling if the measured area of reflected light is lower that a threshold area and the centroid is within a threshold distance from a target location.

In a further embodiment, the image processing means comprises means for recognising a blind microvia as over-drilled or blocked with residual debris if the measured area of reflected light is less than a threshold area and the centroid is greater than a threshold distance from a target location.

Preferably, the camera is telecentric.

In one embodiment, the top lighting means comprises means for generating on-axis or near-on-axis illumination.

In another embodiment, the top lighting means comprises a projection lens for the camera for on-axis top illumination.

In one embodiment, the camera resolution is sufficient for less than 16 $\mu$m object pixel size.

In one embodiment, the robotic system and the board support means comprise means for maintaining a fixed working distance for all measurements.

In another embodiment, the top lighting means comprises means for emitting light in the visible wavelength range.

In one embodiment, the top lighting means further comprises a low-level lighting means for directing light at an angle of less than 40° to the circuit board plane, and the controller comprises means for capturing separate high-level and low-level lighting images and for using the low-level image to define a microvia boundary within which the pixels of the high-level image are processed to determine if the microvia is defective.

In one embodiment, the system further comprises a back lighting means for illuminating a circuit board from the opposite side to that of the camera, and the image processing means comprises means for determining quality of through-microvias according to the location and pattern of light passing through said microvias.

In a further embodiment, the back lighting means comprises an array of LEDs mounted in the circuit board support means to illuminate a fill work space.

In one embodiment, the back lighting means comprises in excess of 4000 LEDs.

In one embodiment, the back lighting means comprises means for activating subsets of LEDs to illuminate the current camera field of view.

In a further embodiment, the board support means comprises a transparent plate, and means for pressing a circuit board against the plate.

In another embodiment, the transparent plate is mounted at a fixed location whereby pressing a circuit board against the transparent plate provides a fixed working distance between the camera and the circuit board.

In one embodiment, the board support means comprises a transparent conveyer mounted beneath the transparent plate, a back lighting means mounted beneath the conveyor, and means for moving the back lighting means upwardly to press against the conveyor so that a circuit board is pressed against the transparent plate.

In a further embodiment, the system comprises a plurality of cameras, and the controller comprises means for controlling capture of images arising from top lighting in one camera and images arising from back lighting in another camera.

In one embodiment, the camera for capturing images from top lighting has a higher resolution than that for capturing images from back lighting.

In a further embodiment, the system comprises a beam splitter mounted to direct light to different cameras.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which.

DETAILED DESCRIPTION OF THE EMBODIMENTS

Figure 1:
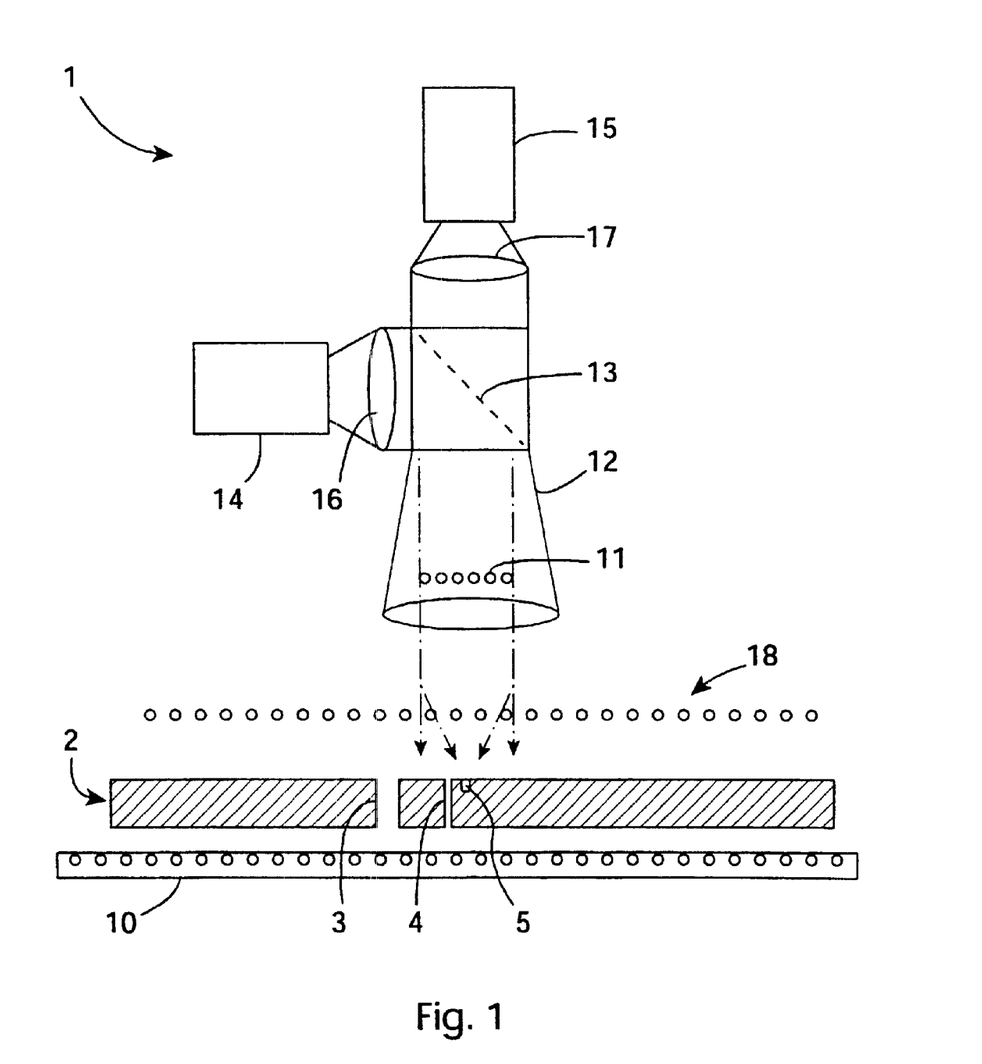
FIG. 1 is a diagrammatic elevational cross-sectional view of an inspection system of the invention.

Referring to FIG. 1, a microvia inspection system 1 of the invention is shown. The system 1 is illustrated inspecting a circuit board 2 having a wide mechanically-drilled through via 3, a laser-drilled through microvia 4 and a laser-drilled blind microvia 5. The system is particularly suitable for detection of defects in through and blind microvias having a diameter in the range of 20 $\mu$m to 200 $\mu$m and a high aspect ratio (length over diameter).

The system 1 comprises a back lighting unit 10 comprising an array of 6000 LEDs of red colour and having an overall power output of 1–5 mW/LED. In general, there should be greater than 4000 LEDs. The back lighting unit 10 comprises a controller for switching sections of LEDs on a configurable basis so that the illumination corresponds to the board panel currently being inspected. The overall workspace illuminated by the back lighting unit 10 is 600 mm×450 mm.

The unit 10 is mounted on a board conveying and supporting mechanism which supports the board 2 in a manner whereby it is maintained flat in a board plane to a tolerance of better than the degree of freedom of the optics. For high resolution, this is typically +/−150 $\mu$m and for low resolution it is typically +/−0.8 mm. In this embodiment, the board 2 is pressed against a fixed sheet of glass, described in more detail below.

The system also comprises a top lighting means comprising on-axis LEDs 11 in a telecentric projection lens 12. The fact that the lens 12 is of the telecentric projection type ensures that there is very comprehensive illumination of the bottom of blind vias. Also, because it is telecentric, the image-side is also on-axis.

Light entering the lens 12 is split by a beam splitter 13 between a high resolution camera 14 and a lower resolution camera 15 via relay lenses 16 and 17 respectively. The cameras 14 and 15 each have a sensor area of 1024×1280 6.7 $\mu$m square pixels. The relay lens 16 provides a magnification value M (image area over object area) of 0.67 giving a resolution dimension of 10 $\mu$m per pixel. In general, the resolution dimension should be less than 16 $\mu$m for blind microvia inspection. Thus for a blind microvia having a diameter of 50 $\mu$m there are 5 pixels across, sufficient for image processing despite the very small size of the microvia. The relay lens 17 provides a magnification value M of 0.27 giving a resolution dimension of 25 $\mu$m per pixel. This resolution is adequate for inspection of the through microvias 3 and 4 using back illumination.

The system 1 also comprises a low-level top lighting unit 18 comprising a ring of red LEDs mounted to direct light at an angle of less than 40° to the board plane.

The lighting unit and the camera assembly is mounted on a robotic gantry system which moves the assembly over the board 2 in a manner whereby the working distance between the lens 12 and the board 2 is constant, in this embodiment 7–8 mm. An optical range finder may be used to ensure uniformity of the working distance using real time feedback. The back lighting LEDs 10 are static as they illuminate the whole workspace.

Figure 2:
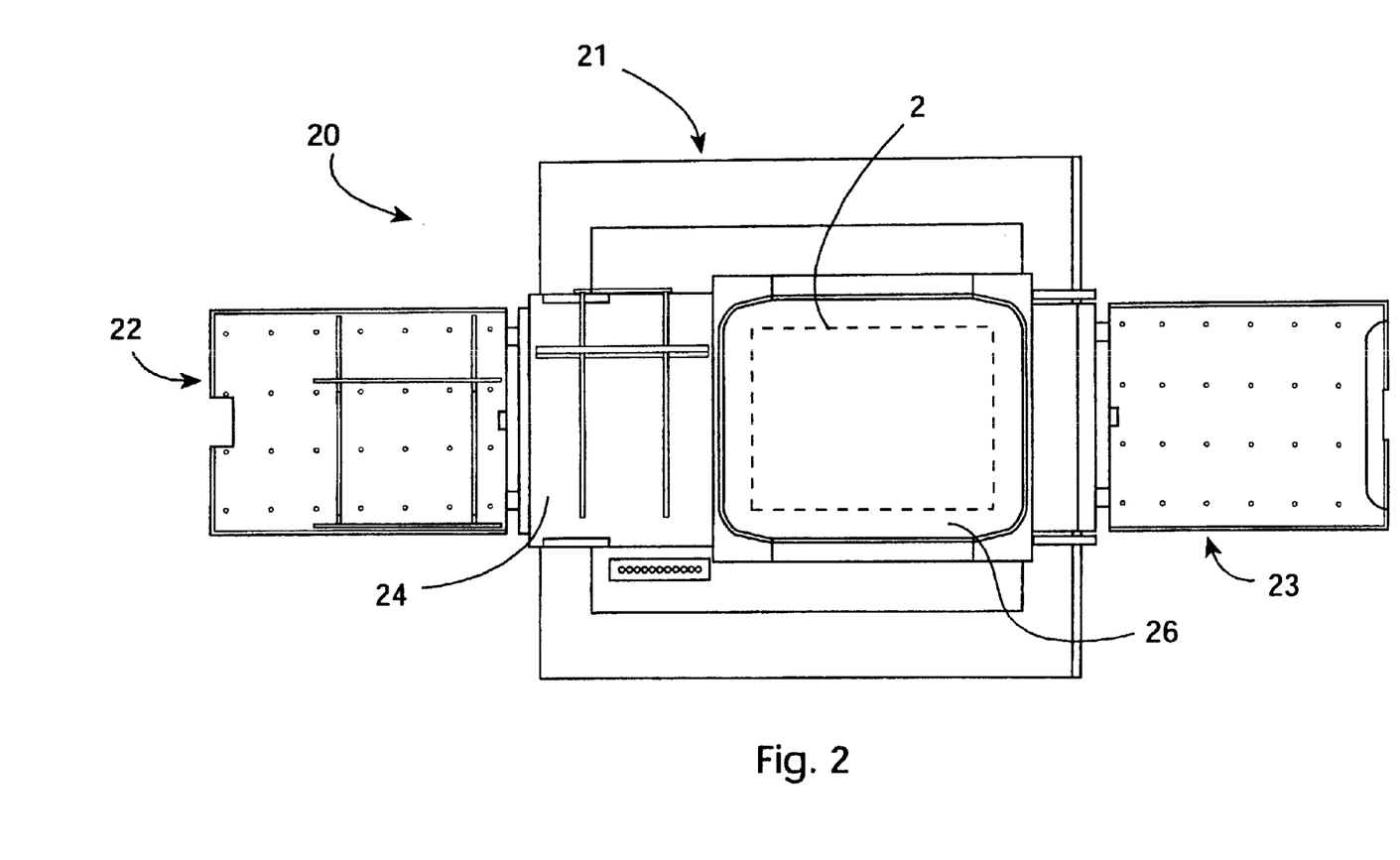
FIG. 2 is a plan view of a handling system of the inspection system.
Figure 3:
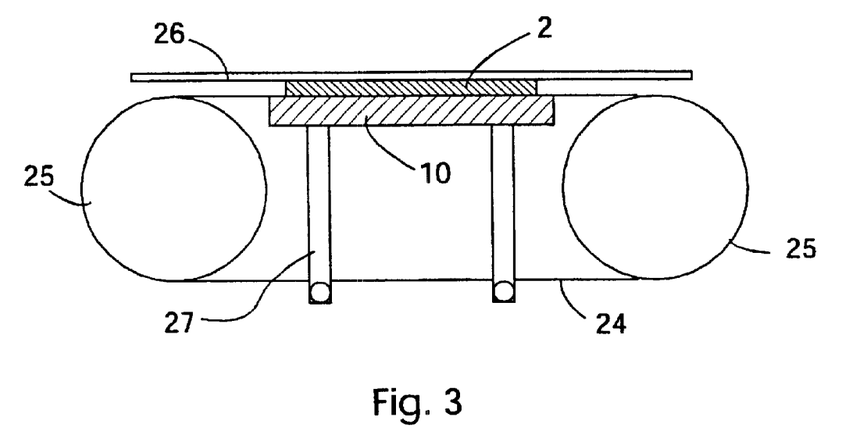
FIGS. 3 and 4 are diagrams illustrating board positioning.
Figure 4:
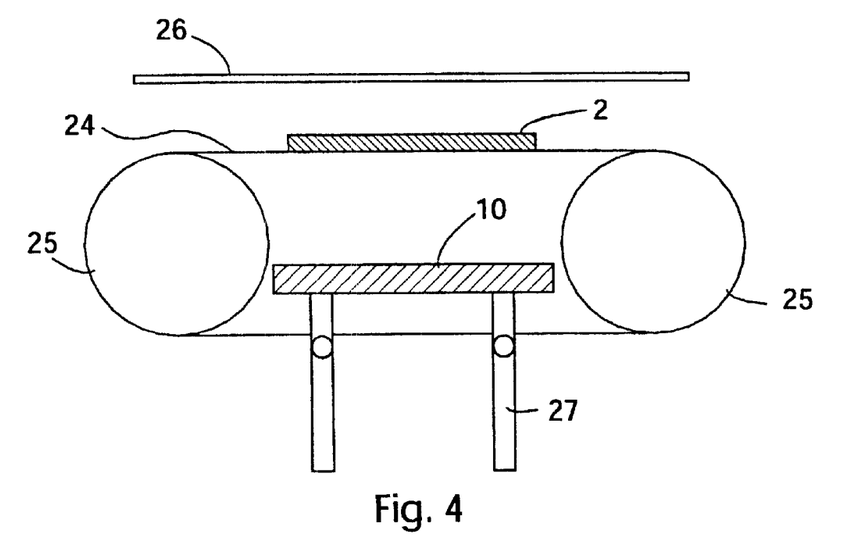

Referring to FIGS. 2 to 4, a board handling system 20 is illustrated. The system 20 comprises a table 21, an input hander 22, and an output handler 23. Between the handlers 22 and 23 and over the table 21, a transparent conveyor 24 is driven by rollers 25. The back lighting unit 10 is mounted on pneumatic pistons 27 on each side of the transparent conveyor 24. A glass plate 26 is mounted in a fixed position over the transparent conveyor 24.

As shown in FIGS. 3 and 4, when a board 2 is conveyed into position on the conveyor 24 from the input handler 22, the back lighting unit 10 is moved upwardly to press the board 2 against the glass plate 26. The back lighting unit LEDs are activated to provide back illumination in synchronism with movement of the top lighting and camera assembly. This illumination passes through the transparent conveyor 24, through the through-microvias and through the glass plate 26. Because the glass plate 26 is fixed there is excellent uniformity of the working distance (WD) to the required tolerance.

Figure 5:
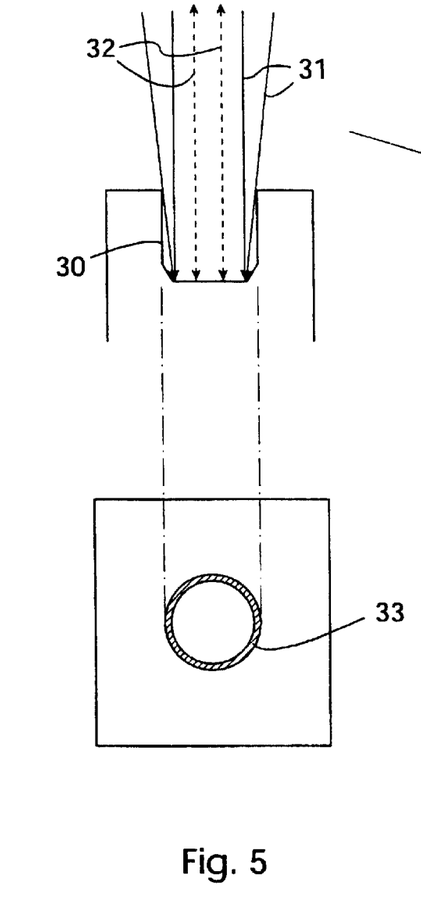
FIGS. 5 and 6 each are diagrammatic elevational and plan views illustrating microvia illumination and the resultant images.

Regarding the top lighting, FIG. 5 illustrates the manner in which a blind microvia 30 is illuminated. On-axis and near-on-axis light 31 penetrates to the bottom of the microvia 30 and reflected light 32 is directed on-axis back to the (telecentric) lens 12. An ideal image 33 is also shown in FIG. 5. There is full reflection from the bottom of the microvia 30 because of reflection from the copper conductor to which an electrical connection is to be made. The shoulder at the bottom of the microvia 30 is dark and so the ideal image 33 has a dark ring. If the design data does not specify such a shoulder there should not be such a ring.

Figure 6:
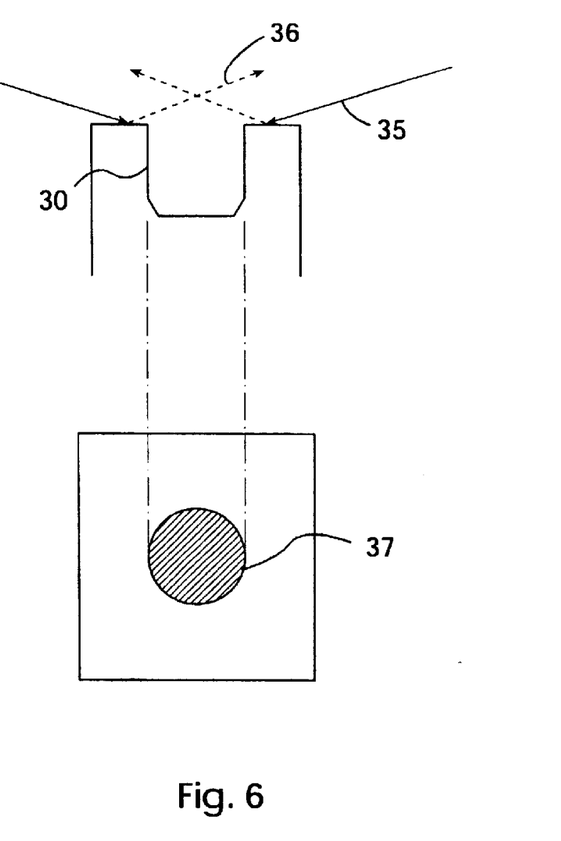
Figure 7:
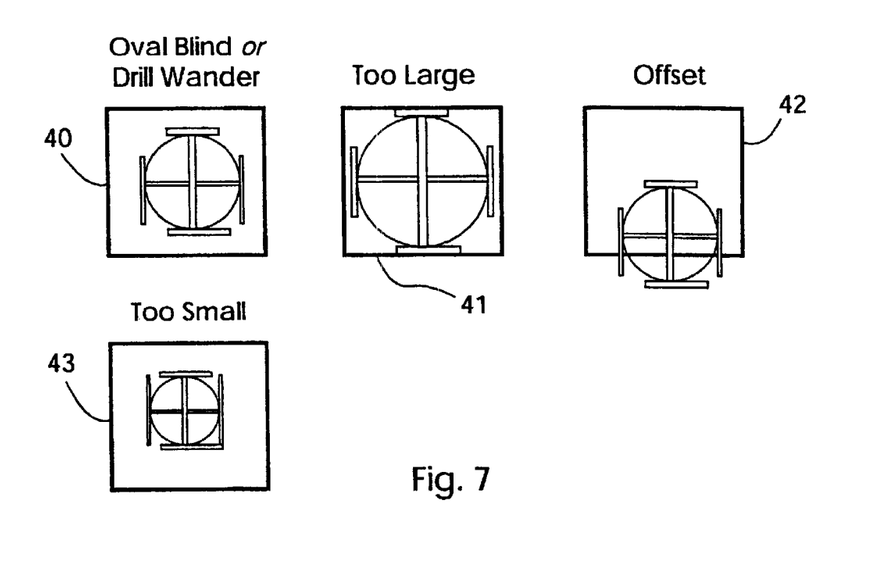
FIGS. 7 and 8 illustrate typical microvia defects.

Referring to FIG. 6, the low-level top lighting unit 18 emits light 35 which does not penetrate to the bottom of the microvia. Therefore reflected light 36 originates only from the surrounding board top surface. The microvia 30 is therefore seen as a dark disc 37.

The system 1 also comprises a controller which directs the robotic system to move the camera/top lighting assembly over the work space, activates the LEDs 11, 18, and 10, and activates the cameras 14 and 15 to capture the respective images. The high resolution camera 14 sequentially captures images originating from low level and high level top lighting, and the camera 15 captures images originating from back lighting.

The controller also comprises an image processor to process these images to recognise defective microvias. Operation of the image processor is best explained with reference to examples illustrated in FIGS. 7 to 10. In FIG.

7, an image 40 is shown for oval blind or drill wander defects. The drill wander defect is shown at 48 in FIG. 8. Another simple type of defect is a microvia having too large a diameter as shown at 41 in FIG. 7. This is clearly discernible with either low level or high level top lighting and in both cases the image is too large. Likewise, either type of top lighting will allow the image processor to recognise an offset microvia 42 or a microvia 43 which is too small.

Figure 8:
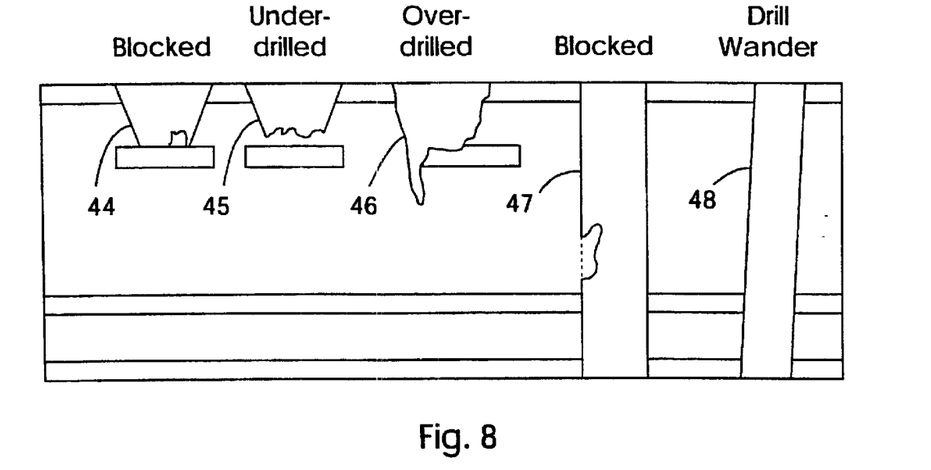

However, other types of defects are not so easily discernible. In FIG. 8 a blocked microvia 44 has residual debris at the bottom. An under-drilled microvia 45 arises if the drilling does not reach a sufficient depth. An over-drilled microvia 46 arises if board material is removed to a greater depth than specified for some or all of the drill area. In FIG. 8, the copper layers are illustrated as the horizontal bands.

FIG. 8 also shows defects in through microvias. A partially blocked microvia 47 has residual debris lodged at a location along its length. A microvia 48 is not perpendicular to the board plane because there was "drill wander".

Figure 9:
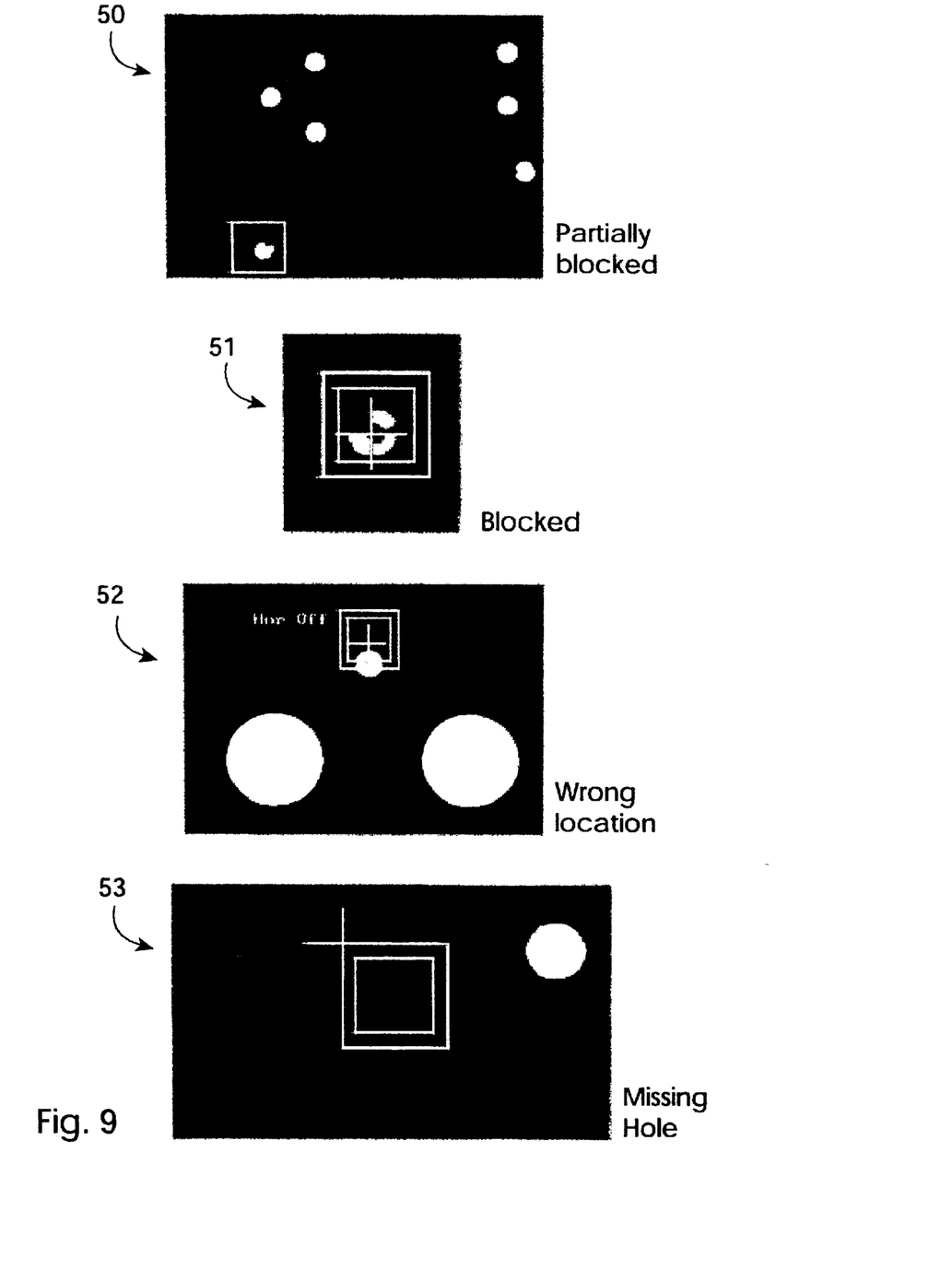
FIG. 9 is a set of images of defective microvias.

FIG. 9 illustrates images 50, 51, 52, and 53 of defective through microvias. These comprise light which passes through the microvias from the back lighting LEDs 10. In the image 50 the lower left microvia is partially blocked, and an example of such a defect is shown at 47 in FIG. 8. An image 51 for a larger blockage is shown. The image processor recognises blockages if the measured area is below a threshold, typically 80% of the ideal. An image 52 includes light from an offset microvia. The image processor recognises this because the centroid of the image is offset greater than a threshold distance from the ideal location. Where there is no image within a search area radius from the ideal location, the image processor determines that the microvia does not exist, as is the case for an image 53.

Figure 10:
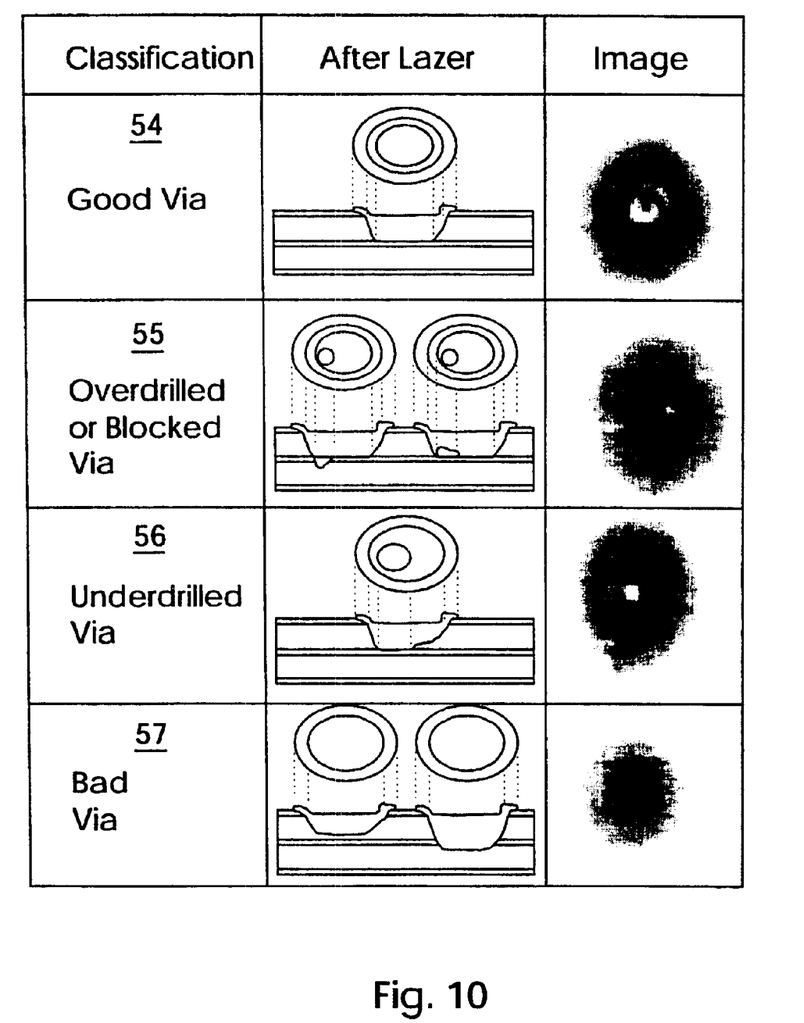
FIG. 10 is a table of image processing criteria and image samples.

Referring to FIG. 10, for blind microvias, a "good" classification 54 in the image processor arises if the pixels have an area above a minimum threshold and if the centroid is less than a threshold distance from the ideal location. A sample image is shown. An "over-drilled" or "blocked" classification 55 arises if the measured area is lower than the area threshold and the centroid is further than the threshold distance from the ideal location. An "underdrilled" classification 56 arises if the measured areas is below the threshold area and the centroid is within the threshold distance from the ideal location. A "bad" classification arises if the measured area is considerably below the area threshold. The centroid, if one exists, is immaterial to this classification.

In the image processing for these classifications, the image processor uses an image from low level top lighting (as shown in FIG. 6) to define the area to be measured. This significantly improves accuracy for difficult classification cases.

It will be appreciated that the system 1 provides for comprehensive inspection of both blind and through microvias without the need for complex equipment. All of the illumination and camera parts are readily available separately. The system allows immediate feedback to a drilling station of defects in real time so that appropriate corrective action can be taken in a timely manner.

It is envisaged that for more comprehensive inspection the top lighting means may include a UV light source for illumination of residual board resin debris in microvias. It is also envisaged that the system may comprise only a back lighting means where only through holes are to be inspected.

The invention is not limited to the embodiments described, but may be varies in construction and detail within the scope of the claims.

What is claimed is:

1. A microvia inspection system comprising:
   means for supporting a circuit board in a circuit board plane;
   a top lighting means comprising means for illuminating the top of a circuit board at an angle of greater than 50° to the circuit board plane;
   a camera;
   a controller comprising:
      means for reading circuit board target data to determine target locations and sizes of microvias, and for controlling the top lighting means and the camera to capture images of said microvias, and image processing means for determining quality of the microvias according to intensity and distribution of reflected light in the images, the image processing means comprising means for recognizing a blind microvia as defective if a measured area of reflected light is below a threshold area.

2. A system as claimed in claim 1, wherein the image processing means comprises means for recognising a blind microvia as defective if a measured centroid of the reflected light is offset from a target location to an extent greater than a threshold distance.

3. The system as claimed in claim 1, wherein the image processing means comprises means for recognising a microvia as defective because of under-drilling if the measured area of reflected light is lower than that of a threshold area and the centroid is within a threshold distance from a target location.

4. The system as claimed in claim 1, wherein the image processing means comprises means for recognising a blind microvia as over-drilled or blocked with residual debris if the measured area of reflected light is less than a threshold area and the centroid is greater than a threshold distance from a target location.

5. The system as claimed in claim 1, wherein the camera is telecentric.

6. The system as claimed in claim 1, wherein the camera resolution is sufficient for less than 16 μm object pixel size.

7. The system as claimed in claim 1, wherein the board support means comprises means for maintaining a fixed working distance for all measurements.

8. The system as claimed in claim 1, wherein the top lighting means comprises means for emitting light in the visible wavelength range.

9. The system as claimed in claim 1, wherein the system further comprises a back lighting means for illuminating a circuit board from the opposite side to that of the camera, and the image processing means comprises means for determining quality of through-microvias according to the location and pattern of light passing through said microvias.

10. The system as claimed in claim 9, wherein the back lighting means comprises an array of LEDs mounted in the circuit board support means to illuminate a full work space.

11. The system as claimed in claim 9, wherein the back lighting means comprises in excess of 4000 LEDs.

12. The system as claimed in claim 9, wherein the back lighting means comprises means for activating subsets of LEDs to illuminate the current camera field of view.

13. The system as claimed in claim 9, wherein the system comprises a plurality of cameras, and the controller comprises means for controlling capture of images arising from top lighting in one camera and images arising from back lighting in another camera.

14. The system as claimed in claim 13, wherein the camera for capturing images from top lighting has a higher resolution than that for capturing images from back lighting.

15. The system as claimed in claim 13, wherein the system comprises a beam splitter mounted to direct light to different cameras.

16. A microvia inspection system comprising:
means for supporting a circuit board in a circuit board plane;
a top lighting means comprising means for illuminating the top of a circuit board at an angle of greater than 50° to the circuit board plane;
a camera;
a controller comprising:
  means for reading circuit board target data to determine target locations and sizes of microvias, and for controlling the top lighting means and the camera to capture images of said microvias, and image processing means for determining quality of the microvias according to intensity and distribution of reflected light in the images;
wherein the image processing means comprises means for recognising a blind microvia as defective if a measured area of reflected light is below a threshold area;
wherein the image processing means comprises means for recognising a blind microvia as defective if a measured centroid of the reflected light is offset from a target location to an extent greater than a threshold distance;
wherein the image processing means comprises means for recognising a microvia as defective because of under-drilling if the measured area of reflected light is lower that a threshold area and the centroid is within a threshold distance from a target location; and
wherein the image processing means comprises means for recognising a blind microvia as over-drilled or blocked with residual debris if the measured area of reflected light is less than a threshold area and the centroid is greater than a threshold distance from a target location.

17. A microvia inspection system comprising:
means for supporting a circuit board in a circuit board plane;
a top lighting means comprising means for illuminating the top of a circuit board at an angle of greater than 50° to the circuit board plane;
a camera;
a controller comprising:
  means for reading circuit board target data to determine target locations and sizes of microvias, and for controlling the top lighting means and the camera to capture images of said microvias, and image processing means for determining quality of the microvias according to intensity and distribution of reflected light in the images; and
wherein the top lighting means further comprises a low-level lighting means for directing light at an angle of less than 40° to the circuit board plane, and the controller comprises means for capturing separate high-level and low-level lighting images and for using the low-level image to define a microvia boundary within which the pixels of the high-level image are processed to determine if the microvia is defective.

18. A microvia inspection system comprising:
means for supporting a circuit board in a circuit board plane;
a top lighting means comprising means for illuminating the top of a circuit board at an angle of greater than 50° to the circuit board plane and means for generating on-axis or near-on-axis illumination;
a camera;
a controller comprising:
  means for reading circuit board target data to determine target locations and sizes of microvias, and for controlling the top lighting means and the camera to capture images of said microvias, and image processing means for determining quality of the microvias according to intensity and distribution of reflected light in the images;
the top lighting means comprising a projection lens for the camera for on-axis top illumination.

19. A microvia inspection system comprising:
means for supporting a circuit board in a circuit board plane;
a top lighting means comprising means for illuminating the top of a circuit board at an angle of greater than 50° to the circuit board plane, the top lighting means further comprising a low-level lighting means for directing light at an angle of less than 40° to the circuit board plane;
a camera;
a controller comprising:
  means for reading circuit board target data to determine target locations and sizes of microvias, and for controlling the top lighting means and the camera to capture images of said microvias, and image processing means for determining quality of the microvias according to intensity and distribution of reflected light in the images,
the controller comprising means for capturing separate high-level and low-level lighting images and for using the low-level image to define a microvia boundary within which the pixels of the high-level image are processed to determine if the microvia is defective.

20. A microvia inspection system comprising:
means for supporting a circuit board in a circuit board plane, the board support means comprising a transparent plate, and means for pressing a circuit board against the plate, the board support means also comprising a transparent conveyer mounted beneath the transparent plate, a back lighting means mounted beneath a conveyor, and means for moving the back lighting means upwardly to press against the conveyor so that a circuit board is pressed against the transparent plate;
a top lighting means comprising means for illuminating the top of a circuit board at an angle of greater than 50° to the circuit board plane;
a camera;
a controller comprising:
  means for reading circuit board target data to determine target locations and sizes of microvias, and for controlling the top lighting means and the camera to capture images of said microvias, and image processing means for determining quality of the microvias according to intensity and distribution of reflected light in the images.

21. The system as claimed in claim 20, wherein the transparent plate is mounted at a fixed location whereby pressing the circuit board against the transparent plate provides a fixed working distance between the camera and the circuit board.

* * * * *